United States Patent [19]

Klein et al.

[11] Patent Number: 5,002,558

[45] Date of Patent: Mar. 26, 1991

[54] ADJUSTABLE URETHRAL CATHETER AND METHOD FOR TREATING OBSTRUCTIVE PROSTATISM

[75] Inventors: Lester A. Klein, Del Mar; Robert F. Rosenbluth, Laguna Niguel; Jay A. Lenker, Laguna Beach; Barry M. Calvarese, Cardiff, all of Calif.

[73] Assignees: The Beth Israel Hospital Association, Boston, Mass.; Advanced Surgical Intervention, Inc., San Clemente, Calif.

[21] Appl. No.: 397,579

[22] Filed: Aug. 23, 1989

[51] Int. Cl.$^5$ ............................................. A61M 29/02
[52] U.S. Cl. ................................... 606/192; 604/101; 604/102; 604/263
[58] Field of Search .................. 128/207.14, 207.15, 128/DIG. 25; 600/29, 31; 604/96–103, 54, 263, 264, 280; 606/7, 191–198

[56] References Cited

U.S. PATENT DOCUMENTS

| 550,238 | 11/1895 | Allen, Jr. . | |
|---|---|---|---|
| 2,799,273 | 7/1957 | Oddo | 604/101 |
| 2,849,002 | 8/1958 | Oddo | 604/101 X |
| 2,936,760 | 5/1960 | Gants . | |
| 3,332,424 | 7/1967 | Minteer | 604/280 X |
| 3,977,408 | 8/1976 | MacKew . | |
| 4,022,191 | 5/1977 | Jamshidi | 604/263 X |
| 4,141,364 | 2/1979 | Schultze . | |
| 4,149,539 | 4/1979 | Cianci | 604/97 X |
| 4,205,691 | 6/1980 | Patel . | |
| 4,219,026 | 8/1980 | Layton . | |
| 4,311,146 | 1/1982 | Wonder . | |
| 4,315,512 | 2/1982 | Fogarty | 604/97 X |
| 4,346,698 | 8/1982 | Hanson et al. | 604/103 X |
| 4,349,033 | 9/1982 | Eden | 604/96 X |
| 4,432,757 | 2/1974 | Davis, Jr. . | |
| 4,572,186 | 2/1986 | Gould et al. | 604/99 X |
| 4,660,560 | 4/1987 | Klein | 604/101 X |
| 4,932,958 | 6/1990 | Reddy et al. | 606/192 |

FOREIGN PATENT DOCUMENTS 8102109 8/1981 PCT Int'l Appl. ................. 604/96

OTHER PUBLICATIONS

Klein, L., M.D., and Abrams, P., M.D. *Transurethral Cystoscopic Balloon Dilatation of the Prostate*, Problems in Urology, Jul.–Sep. 1989, vol. 3, No. 3, pp. 395–402.

*Primary Examiner*—John D. Yasko
*Assistant Examiner*—Adam J. Cermak
*Attorney, Agent, or Firm*—Lorusso & Loud

[57] ABSTRACT

A urethral catheter having an adjustable dilating balloon length for dilating a prostatic urethra and a method for using same. The device includes a catheter to which a Foley balloon is affixed at the distal end, and to which a dilating balloon is annularly affixed, and includes means to independently expand and contract the balloons. Concentrically encompassing the catheter is a sheath or ring, which in one embodiment slides along the outside of the catheter. With the method of the present invention, the affected prostatic urethra is measured using a cystoscope and a calibrated catheter or other known measurement means. The sheath of an adjustable catheter of one embodiment of the present invention is set to the measured length by covering a portion of the dilating balloon with the sheath. The dilating catheter is inserted through the urethra until the balloon at the distal end is located within the bladder, at which point it is inflated and the dilating catheter is anchored in position. Then the dilating balloon is inflated to force the prostate away from the urethra. The dilating balloon may be left in place for periods of up to an hour or more to optimize the dilation effect, at which point the balloons are deflated and the dilating catheter is removed. With a further embodiment, the length of the dilating balloon is adjusted by severing portions of an adjustable length sheath to expose the length of balloon desired.

9 Claims, 2 Drawing Sheets

ADJUSTABLE URETHRAL CATHETER AND METHOD FOR TREATING OBSTRUCTIVE PROSTATISM

BACKGROUND OF THE INVENTION

The present invention relates to treatment of obstructive prostatism, and more particularly to an adjustable urethral catheter for treating prostatism and a method for using same.

The present invention is specifically directed to an improvement in the method and the balloon catheters disclosed in U.S. Pat. No. 4,660,560 entitled, Method for Treating Obstructive Prostatism, to Klein, which is assigned to the assignee of the present application. The teachings of U.S. Pat. No. 4,660,560 are specifically incorporated herein by reference.

Obstruction of the urinary tract due to compression of the urethra by an enlarging prostate gland results in a number of symptoms in the patient, including nocturia, frequent urination, stranguria and post-void dribbling, as well as the emotional problems of pain, discomfort and embarrassment. Generally, patients suffering from such symptomatic prostatism may pursue one of three options: Continue living with the pain and discomfort, undertake prostatectomy surgery, or receive treatment by means of a urethral catheter. Choosing the surgical procedure subjects the patient to a number of hazards, including post-operative bleeding, stricture formation at the urethra or bladder neck, incontinence, post-manipulation pain or bladder spasm, urinary infection, reactive urethral swelling causing urinary obstruction and epididymitis. Further risks include wound infection, retention of prostatic chips, retrograde ejaculation, bladder perforation, hyponatremia, intravascular hemolysis, and impotency. Additionally, simple prostatectomy requires at least 1 to 3 hours in the operating room, followed by an average of one week in the hospital, and in complicated cases, two or more weeks. About 10 to 15% of prostatectomy patients require a repeat prostatectomy and probably 10% develop strictures with long-term cost considerations.

Conversely, choosing to abstain from surgery neither alleviates the patient's pain or discomfort nor reduces the probability that more serious prostate problems will develop in the future.

The third option available, that of receiving treatment by means of a urethral catheter, has a number of advantages over the above-mentioned options. Treatment by means of a urethral catheter is disclosed in the following patents: Kealing U.S. Pat. No. 3,997,408; Gants U.S. Pat. No. 2,936,760; and Layton U.S. Pat. No 4,219,026. The present invention is directed to an improvement in the procedure and balloon catheter disclosed in Klein U.S. Pat. No. 4,660,560. In the procedure set forth in that patent, a balloon on a catheter is utilized to apply pressure against the prostate gland, forcing the gland into a position from which it can no longer restrict the urethra.

In using the method described in U.S. Pat. No. 4,660,560 it is necessary that the balloon that is utilized to dilate the prostatic urethra have an annular length and be positioned so that it exerts pressure along the entire surface of the prostate gland, and not beyond the prostate gland. If the balloon is longer than the urethra, damage to the area outside of the prostatic urethra will result when the balloon is expanded. Conversely, if the balloon is shorter than the urethra, the entire obstructed area will not be expanded and obstruction will remain. For this reason, the length of the patient's urethra which is encircled by the prostate gland must be measured, preferably with a calibrated catheter. A dilating catheter which has a dilating balloon of an annular length equal to the measured length of the patient's prostate gland must then be selected. Since the size of the prostate gland to be treated varies from patient to patient, it is necessary that an extensive stock of catheters having varying balloon lengths be kept on hand. Thus, an expanded inventory of catheters is necessary and results in the expenses associated with carrying such a large inventory.

Accordingly, a primary object of the present invention is to provide a balloon catheter which has the capability of being adjusted so that it can be aligned in the urethra to coincide with the length of the urethra surrounded by the prostate gland.

Another object of the present invention is to eliminate the need for keeping an inventory of various sized balloon catheters in order to perform the dilating procedure set forth in U.S. Pat. 4,660,560.

Still another object of the present invention is to provide a method for adjusting the balloon length in a urethral catheter.

A further object of the present invention is to provide a single catheter which can be utilized to dilate a prostate gland regardless of the size or location of the prostate gland.

SUMMARY OF THE INVENTION

These and other objects of the present invention are met by providing a urethral catheter having an adjustable dilating balloon and a method for using that catheter. The catheter used in the present invention includes a Foley balloon at its distal end and an adjustable dilating balloon adjacent the Foley balloon at the distal end of the catheter.

In a preferred embodiment, the adjustable urethral catheter is used with known devices as follows. A multi-channel cystoscope is inserted through the urethra up into the bladder. A calibrated catheter of conventional design is inserted through the cystoscope and urged upwards until it reaches the bladder. A Foley-type balloon located on the distal end of the calibrated catheter is expanded. The calibrated catheter is then slightly withdrawn in order to anchor the balloon and the calibrated catheter to the neck of the bladder. The cystoscope is then withdrawn until the optical piece is located immediately below the prostate gland. The calibration marks on the calibrated catheter are then visually discernible and the length between the neck of the bladder and the veru montanum is easily measured. The balloon on the calibrated catheter is then deflated and the calibrated catheter is withdrawn. A second catheter used is the dilating catheter of the present invention. The dilating catheter also has a Foley-type balloon at the distal end, and further has a remotely fixed annular balloon. The annular length of the annular balloon is adjusted in one embodiment by means of a sliding sheath so that the annular length equals the length of the just-measured prostatic urethra to be treated. The dilating catheter is inserted through the urethra until the distal balloon is located within the bladder. The distal balloon is then inflated and the catheter withdrawn until it engages the bladder neck, fixedly positioning the annular balloon with respect to the prostatic gland. The annular balloon located along the length of the affected prostate gland is then inflated, and the prostate is forced away from the urethra. The dilating balloon may be left in place for periods of up to an hour or more in order to optimize the dilation effect upon the urethra. Subsequent to reaching the desired urethral dilation, both the anchoring distal balloon and the expanded remote annular balloon are deflated and the catheter is withdrawn from the patient's urethra. With a further embodiment, the length of the dilating balloon is adjusted by severing portions of an adjustable length sheath to expose the length of balloon desired.

The present invention is further described in the following description of the preferred embodiments taken together with the drawing, in which like reference numbers refer to like members in the various figures.

DESCRIPTION OF THE PREFERRED EMBODIMENTS

Figure 1:
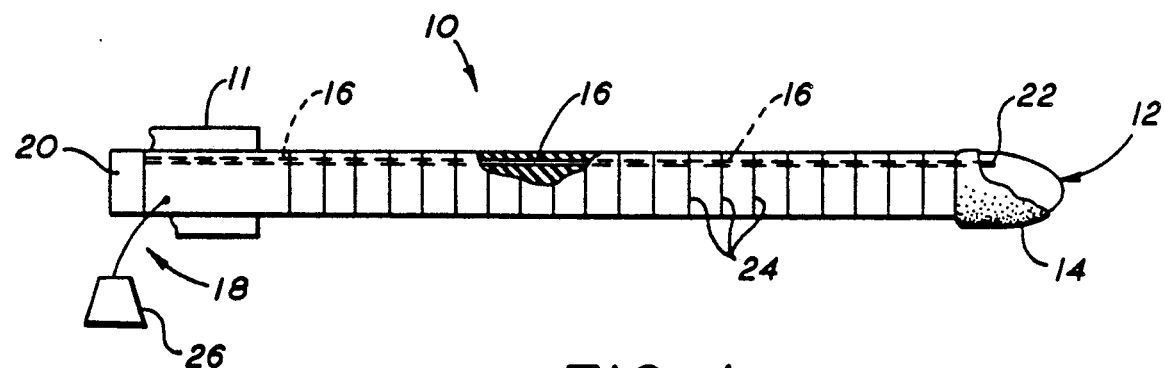
FIG. 1 is a perspective view in partial section of the calibrated catheter used to measure the length of the prostatic urethra prior to performing the method of the present invention.

At the outset the invention is described in its broadest overall aspects with a more detailed description following. In its broadest overall aspects, the present invention utilizes a balloon catheter 50 to treat a prostate gland, which balloon catheter includes a dilating balloon 54 which is adjustable in length so as to coincide with the length of the prostate gland that surrounds the urethra. The catheter 50 containing the adjustable dilating balloon 54 has attached to its distal end 52 a Foley balloon 53 which is herein referred to as the distal balloon. The distal balloon 53 is expanded by means of a hole 64 in the catheter 50. The dilating balloon 54 is annularly affixed to the catheter 50 and is expanded by means of a second hole 62 in the catheter. The source of expansion for each balloon is independent so that each balloon may be expanded and contracted independently from the other balloon. Concentrically encompassing the catheter 50 is a sheath 74, which slides along the outside of the catheter.

In a preferred embodiment, the adjustable urethral catheter 50 is used as follows. First, the length of the urethra to be treated for obstruction by the prostate gland is measured using a known method, such as the method disclosed in U.S. Pat. No. 4,660,560. The annular length of the annular balloon 54 is adjusted by means of the sliding sheath 74 so that the annular length equals the length of the just-measured prostatic urethra to be treated. Once properly positioned, the sliding sheath 74 is secured so that inflation of the annular balloon 54 does not cause the sliding sheath 74 to move. While the sliding sheath 74 can be secured in several ways, one such method would be to use a biocompatible glue such as is known in the art. The dilating catheter 50 is inserted through the urethra until the distal balloon 53 is located within the bladder. The distal balloon 53 is then inflated and the catheter 50 is withdrawn until the distal balloon engages the bladder neck, fixedly positioning the catheter and the annular balloon 54 with respect to the prostatic gland. The annular balloon 54 located along the length of the prostatic urethra to be treated is then inflated, and the prostate is forced away from the urethra.

The dilating balloon 54 may be left inflated and in place for periods of up to an hour or more in order to optimize the dilation effect upon the urethra. Subsequent to reaching the desired urethral dilation, both the anchoring distal balloon 53 and the expanded remote annular balloon 54 are deflated and the catheter is withdrawn 54 from the patient's urethra.

In one important embodiment of the invention the length and location of the prostate gland are determined in accordance with the calibrating technique set forth in Klein U.S. Pat. No. 4,660,560. With that technique, a calibrating catheter 10 is inserted into the urethra and a determination of the length and location of the prostate gland is made by anchoring the calibrating catheter 10 in the neck of the bladder with an expanded Foley balloon 14 and reading calibration markings 24 on the catheter through an optical piece (not shown). However, it is to be understood that the present invention is directed to a dilating catheter 50 and a procedure for dilating the prostate gland. Thus the exact method and apparatus used for determining the length and position of the prostatic urethra to be treated forms no part of the present invention. For example, that information can be determined by X-ray techniques well within the skill of those in the art. To understand the invention the following description is made with reference to the use of a calibrating catheter 10 as shown in FIG. 1.

With the method of the present invention, a conventional calibrated catheter 10 as shown in FIG. 1, is received through a multichannel cystoscope 11, and includes a distal end 12 upon which a Foley-type balloon 14 is fixed. Hereinafter, the Foley-type balloon 14 will be referred to as the distal balloon. Conduit 16 extends through and along the length of the calibrated catheter from the distal end 12 to a proximal end 18 where it terminates into a dual valve 20 in communication with a liquid cystokon supply (not shown). Activating dual valve 20 initiates fluid flow which travels from the proximal end 18 to the distal end 12 of calibrated catheter 10 through the conduit 16, and then progresses down the path of least resistance through hole 22 communicating with the interior of distal balloon 14 which expands relative to the fluid velocity and volume. In an alternative embodiment, various types of fluid or gas may be used to inflate the Foley-balloon 14. Such procedures are known to those skilled in this art. Calibration marks 24 extending along the exterior face of the calibrated catheter 10 are read from the distal end 12 to the proximal end 18, and since it is the distal end 12 which will be fixedly positioned adjacent to the bladder neck, the readings enable measurement of the prostatic gland length. The distance separating each calibrating indicia 24 is dependent upon the measurement system selected, with quarter of an inch increments being used in a preferred embodiment.

The use of the conventional calibrated catheter 10 in the method of the present invention commences with the insertion of the distal end 12 into the penile meatus 84 through the urethra 86 and into the bladder. Depending upon the patient's sensitivity and his extent of prostatic pain, local anesthesia may be required at this time. Subsequent to the distal end 12 entering the bladder, valve 20 is activated enabling the conduit 16 to communicate with the liquid cystokon supply (not shown) thereby inflating the distal balloon 14 inside the bladder. Closing valve 20 halts the flow of liquid both to and from the distal balloon 14, remotely sealing the inflated balloon inside the bladder. The calibrated catheter 10 is slowly withdrawn until the distal balloon 14 lodges in the bladder neck 92. A simple weight 26 or other means of tensing the catheter may be removably fixed to the proximal end 18 in order to securely maintain engagement of the distal balloon 14 to the bladder neck 92. Withdrawing the multichannel cystoscope 11 until its lens is positioned directly below the prostate facilitates reading the calibrating indicia 24. Adding the number of calibrations 24 extending between the bladder neck 92 and veru montanum 94 will result in a measurement corresponding to the length of the affected prostatic urethra and will additionally serve as the length to which the remotely fixed annular dilating balloon 54 of the dilating catheter 50 is set (see FIG. 3). Releasing the liquid cystokon through valve 20 deflates the distal balloon 14, enabling removal of the calibrated catheter 10 once an accurate and satisfactory measurement of the length of the prostatic urethra to be treated has been completed.

Figure 2:
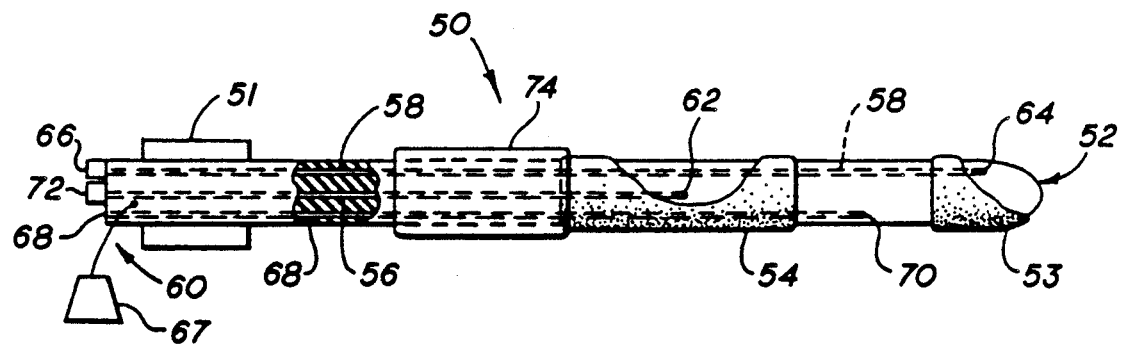
FIG. 2 is a perspective view of the adjustable urethral catheter of the present invention, in which the sheath is shown drawn away from the dilating balloon.
Figure 5:
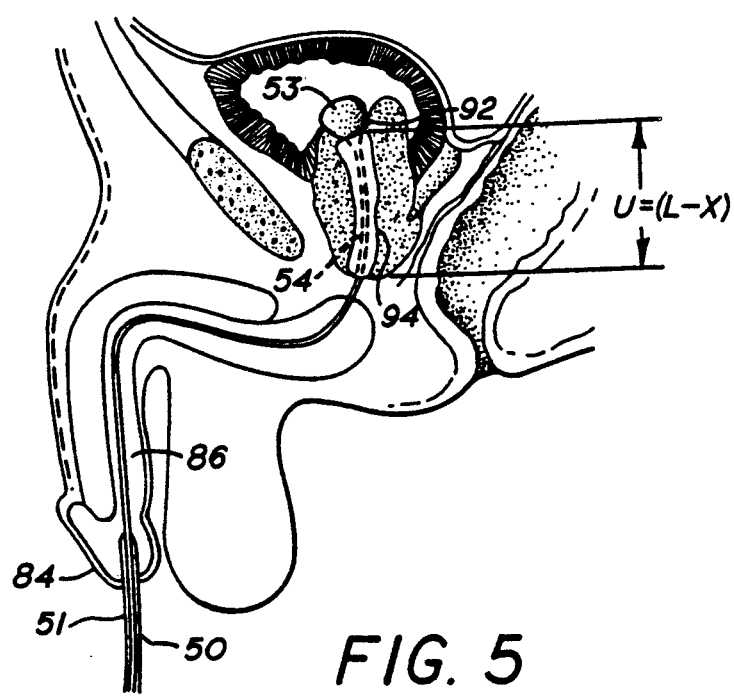
FIG. 5 is a cross-sectional view of the adjustable urethral catheter of the present invention as applied to the male urinary tract.
Figure 3:
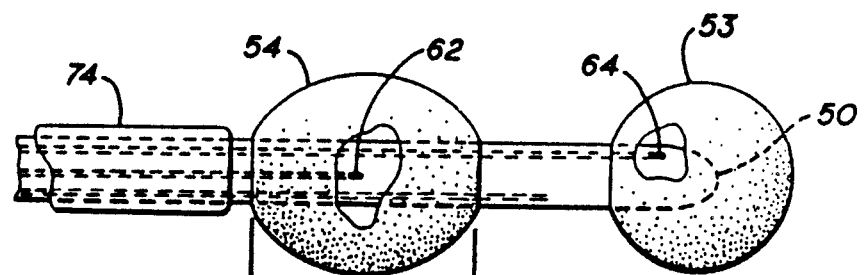
FIG. 3 is a perspective view of the adjustable urethral catheter of FIG. 2, in which the sheath is shown withdrawn to allow full expansion of the dilating balloon.
Figure 4:
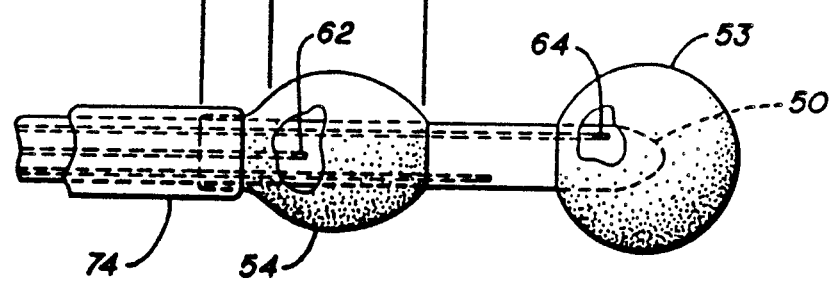
FIG. 4 is a perspective view of the adjustable urethral catheter of FIG. 2, in which the sheath is shown partially constricting the expansion of the dilating balloon.

The dilating catheter 50 of FIG. 2 is utilized to pressure dilate the prostatic urethra. The catheter 50 is inserted through a multichannel cystoscope 51 and includes a distal end 52 upon which a Foley-balloon 53 (hereinafter referred to as the distal balloon) is fixed, and an annular balloon 54 disposed proximate to the distal end 52. A pair of parallel conduits 56 and 58 extend from the proximal end 60, with conduit 56 terminating in hole 62 which is in communication with the annular balloon 54 interior, and conduit 58 terminating in hole 64 which communicates with the distal balloon 53 interior. The exposed length of the annular balloon 54 along the dilating catheter 50 is varied by moving an annular sheath 74 along the catheter. As seen in FIGS. 3 and 4, as the sheath 74 is moved toward the distal end 52, the exposed length of the annular balloon 54 is reduced from its original length L by an amount X, and hence the amount of annular balloon 54 to be inflated is reduced. In this way, the balloon length can be adjusted to equal the length of the affected prostatic urethra and effectively custom fit the dilating catheter 50 to the particular patient being treated. In FIG. 5, the length of the affected prostatic urethra is shown by the letter U, which is equivalent to L-X.

Since the length of the affected prostatic urethra will always be finite, the effective length of the annular balloon need never by reduced by more than L the original length of the annular balloon 54; X<L in all cases. Accordingly, the annular sheath need at most have a length L equal to the length of the annular balloon. By "effective length," as used here and in the claims, is meant the length U of the annular balloon 54 which will be capable of expanding annularly with the sheath in place.

In the preferred embodiment the distal end 52 is received through the cystoscope 51 and urged through the urethra into the bladder. It may be taken for granted that such a procedure is most likely preceded by the application of anesthesia. Valve 66, communicating with the liquid cystokon supply and conduit 58, is slowly opened to inflate the distal balloon 53 now within the bladder. Closing valve 66 remotely seals the distal balloon 53, and a slight withdrawal of the dilating catheter 52 engages the expanded distal balloon 53 to the bladder neck 92, fixedly positioning the annular balloon 54 with respect to the prostatic urethra as defined by the bladder neck 92 and veru montanum 94. Again, a weight 67 may be removably attached to the proximal end 60 in order to maintain the anchoring of the distal balloon 53 to the bladder neck 92. At this time, medication facilitating dilation of the urethra, such as xycocaine, may be injected into conduit 68 and applied to the prostatic urethra through aperture 70 disposed directly above annular balloon 54. Valve 72 is now opened slightly in order to regulate expansion of the annular balloon 54. Subsequent to reaching the desired expansion, valve 72 is closed, remotely sealing the annular balloon 54 and retaining it in a dilating position within and against the urethra. Depending upon the gravity of the prostate encroachment and the related disorder, the annular balloon 54 may be left untouched for periods of up to an hour or more so as to optimize the dilating effect. Since the annular balloon 54 is capable of exerting a pressure of up to 100 psi, it is necessary that the sheath 74 be constructed of a material capable of withstanding such a pressure. Subsequent to attaining sufficient pressure dilation of the urethra, both valves 66 and 72 may be activated to release the liquid cystokon, thereby deflating both the distal balloon 53 and the annular balloon 54 and enabling withdrawal of the dilating catheter 50.

FIG. 5 illustrates a cross-sectional view of the dilating catheter 50 of the present invention as used within the male urinary tract. Multichannel cystoscope 51 is received through penile meatus 84 and lodges in the urethra 86 where it receives the dilating catheter 50 through one of its lumens. Expanded distal balloon 53 is anchored to the bladder neck 92 while annular balloon 54 is fixedly positioned with respect to the prostatic urethra as defined by the bladder neck 92 and veru montanum 94. Pressure dilation of the prostatic urethra by the annular balloon 54 which is adjusted to a length equal to the length U of the prostatic urethra by the annular sheath (not shown) continues as long as is required. In a preferred embodiment, X-ray examination is performed in order to ensure that each component is in the correct location and proper orientation.

Figure 6:
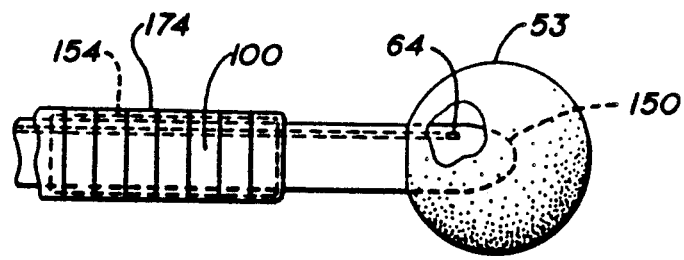
FIG. 6 is a perspective view of a further embodiment of the adjustable urethral catheter of the present invention in which the sheath is of an adjustable length.
Figure 7:
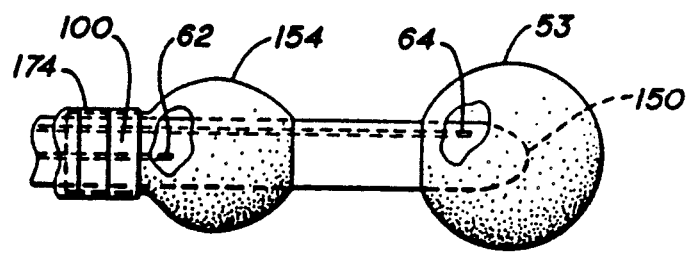
FIG. 7 is a perspective view of the adjustable urethral catheter of FIG. 6 in which segments of the sheath of adjustable length are removed from the sheath to expose the balloon to be expanded.

In a further embodiment of the present invention as shown in FIGS. 6 and 7, the length of the balloon 154 to be expanded is adjusted by means of an adjustable length sheath 174 on the dilating catheter 150. Before use the adjustable length sheath 174 cover the full length of the balloon 154. The sheath 174 may be scored in incremental segments 100 of, for example, 0.5 or 1.0 cm in length. After determining the length of the prostate gland to be treated, segments 100 may be peeled off or broken away from the bulk of the adjustable sheath 174 until the required length of balloon 154 for expansion is exposed. For example, if a prostate of 2 cm is to be expanded and the segments 100 come in 0.5 cm segments, 4 segments are peeled off or broken away to produce an exposed balloon length of 2 cm. The break away embodiment of the adjustable length sheath 174 of the present invention is disclosed to illustrate one method of providing an adjustable length sheath. Other methods include sawing or otherwise removing measured portions of the sheath 174 to expose the desired balloon length. Since, as discussed above, the sheath 174 will have to be capable of withstanding up to 100 psi of pressure, a preferred embodiment of the invention will be constructed so that the individual segments are attached to one another rigidly enough to withstand this pressure without breaking away from one another. This will typically require that some form of cutting tool be used to separate the segments in order to customize the sheath 174 to the needs of the patient. After adjusting the sheath 174 and hence the balloon 154 to the desired length, the catheter 150 is inserted and the balloon is expanded to dilate the affected prostate.

The embodiments which have been described above are but a few of several which utilize this invention and are set out here by way of illustration but not of limitation. Many other embodiments which will be readily apparent to those skilled in the art may be made without materially departing from the spirit and scope of this invention.

What is claimed is:

1. An apparatus for dilating a prostatic urethra, comprising:
   a urethral catheter having a proximal and a distal end;
   means for anchoring the urethral catheter in a prostatic urethra fixed near the distal end;
   means for expanding the urethral catheter in order to dilate a prostatic urethra disposed proximate to the distal end; and
   means for adjusting the effective length of the means for expanding the urethral catheter disposed proximate to the means for expanding the urethral catheter such that said adjusting means may directly determine the effective length of said expanding means, said means for adjusting the effective length of the means for expanding the urethral catheter having a length not greater than the length of the means for expanding the urethral catheter, said means for adjusting the effective length of the means for expanding the urethral catheter comprising an annular sheath slideably located along the urethral catheter, said annular sheath being capable of withstanding a pressure force generated by the means for expanding the urethral catheter of up to 100 psi.

2. A method of dilating a prostatic urethra, which comprises:
   providing a urethral catheter, having
      a proximal end and a distal end,
      a balloon fixed to the distal end of the urethral catheter,
      an annular balloon fixed to the urethral catheter between the proximal end and the distal end, and
      means for adjusting the effective length of the annular balloon;
   adjusting the annular length of the annular balloon such that it equals the length of the prostatic urethra;
   introducing an endoscopic lens into and along the length of the prostatic urethra;
   passing the urethral catheter substantially parallel to the endoscopic lens into and along the prostatic urethra;
   positioning the annular length of the annular balloon between the adjacent to the bladder neck and the veru montanum; and
   expanding the annular balloon in order to dilate the prostatic urethra and to relieve the prostatic encroachment on the prostatic urethra.

3. A method according to claim 2, wherein the effective length of the annular balloon is adjusted by slideably locating an annular sheath along the urethral catheter.

4. A method according to claim 2, wherein the positioning step comprises:
   passing the balloon fixed to the distal end through the urethra and into the bladder;
   expanding the balloon fixed to the distal end; and
   engaging the expanded balloon to the bladder neck such that the balloon anchors the distal end of the urethral catheter with respect to the prostatic urethra as defined by the bladder neck and the veru montanum.

5. A method of dilating a prostatic urethra, which comprises:
   providing a urethral catheter, having
      a proximal end and a distal end,
      a balloon fixed to the distal end of the urethral catheter;
      an annular balloon fixed to the urethral catheter between the proximal end and the distal end, and
      means for adjusting the effective length of the annular balloon;
   introducing an endoscopic lens into and along the length of the prostatic urethra;
   measuring the distance between the bladder neck and veru montanum;
   adjusting the annular length of the annular balloon such that it equals the length of the prostatic urethra;
   passing the urethral catheter substantially parallel to the endoscopic lens into and along the prostatic urethra;
   positioning the annular length of the annular balloon between and adjacent to the bladder neck and the veru montanum; and
   expanding the annular balloon in order to dilate the prostatic urethra and to relieve the prostatic encroachment on the prostatic urethra.

6. A method of dilating a prostatic urethra as set forth in claim 2, including the step of introducing an endoscopic lens, wherein the endoscopic lens is a multichannel cystoscope.

7. A method of dilating a prostatic urethra as set forth in claim 6, wherein the urethral catheter is passed through a lumen in the cystoscope.

8. A method of dilating a prostatic urethra as set forth in claim 5, including the step of introducing an endoscopic lens, wherein the endoscopic lens is a multichannel cystoscope.

9. A method of dilating a prostatic urethra as set forth in claim 8, wherein the urethral catheter is passed through a lumen in the cystoscope.

* * * * *